(12) United States Patent
Davis et al.

(10) Patent No.: US 8,815,234 B2
(45) Date of Patent: Aug. 26, 2014

(54) TREATMENT OF HUMAN OR ANIMAL BODY SURFACE INFECTION

(75) Inventors: Paul Davis, Bedford (GB); Andrew Austin, Wellingborough (GB)

(73) Assignee: Insense Limited, Bedford (GB)

( * ) Notice: Subject to any disclaimer, the term of this patent is extended or adjusted under 35 U.S.C. 154(b) by 281 days.

(21) Appl. No.: 13/318,241

(22) PCT Filed: Apr. 30, 2010

(86) PCT No.: PCT/GB2010/050721
§ 371 (c)(1),
(2), (4) Date: Oct. 31, 2011

(87) PCT Pub. No.: WO2010/125398
PCT Pub. Date: Nov. 4, 2010

(65) Prior Publication Data
US 2012/0058101 A1    Mar. 8, 2012

(30) Foreign Application Priority Data
May 1, 2009    (GB) .................................. 0907553.2

(51) Int. Cl.
*A61K 38/44* (2006.01)
*C12N 9/08* (2006.01)
*C12N 9/04* (2006.01)

(52) U.S. Cl.
USPC .......................... 424/94.4; 435/192; 435/190

(58) Field of Classification Search
USPC .................................. 424/94.4; 435/192, 190
See application file for complete search history.

(56) References Cited

FOREIGN PATENT DOCUMENTS

| WO | WO 00/28821 A1 | 5/2000 |
| WO | WO 03/047503 A2 | 6/2003 |
| WO | WO 03/090800 A1 | 11/2003 |
| WO | WO 2006/133523 A2 | 12/2006 |
| WO | WO 2008/009925 A2 | 1/2008 |
| WO | WO 2008/041218 A1 | 4/2008 |

OTHER PUBLICATIONS

Lowbury et al., "Use of 4% chlorhexidine detergent solution (Hibiscrub) and other methods of skin disinfection," British Medical Journal 1:510-515, 1973.*

* cited by examiner

*Primary Examiner* — Rosanne Kosson
(74) *Attorney, Agent, or Firm* — DASCENZO Intellectual Property Law, P.C.

(57) ABSTRACT

A method of treatment of a human or animal body surface infection, particularly a fungal infection, comprises applying an aqueous liquid to the infected body surface, e.g. nail region, followed by applying a dressing comprising a source of hydrogen peroxide. Also provided is a combination of the liquid and dressing for use in the method.

21 Claims, 2 Drawing Sheets

TREATMENT OF HUMAN OR ANIMAL BODY SURFACE INFECTION

TECHNICAL FIELD

The present invention relates to the treatment of human or animal body surface infections, particularly a fungal infection of a human nail region.

BACKGROUND

Healthy nails in visibly good condition are important and highly prized aspects of human appearance. Frequently the appearance, strength and health of nails can be adversely affected by infection with pathogenic fungal cells, typically of the genus Trychophyton, and there is a strong demand for therapies that improve the appearance of affected nails by elimination of the infecting fungi. Although there are numerous remedies on the market, there is widespread dissatisfaction with available technologies and products.

Systemically delivered agents can reach the nail region through the blood stream, but poor penetration into the nail region from the circulation and serious side effects limit the usefulness of the approach.

Fungally infected nails are often rendered porous or open by the action of the invading fungi. Thus, often the nail is co-colonised with bacteria which can exacerbate the damaging effects of the fungi by releasing additional destructive enzymes and locally active toxins.

It is well recognised that even if a fungal nail infection is reduced by a known therapy, it is seldom completely eliminated and it is usual for infections to return soon after treatment is stopped.

SUMMARY OF THE INVENTION

The inventors have discovered that the active ingredients do not readily penetrate the nail and little, if any, of the material applied to the top surface reaches the underlying structures where fungal cells can reside in relative safety.

Methods according to the disclosure include methods for treatment of an infected body surface of a human or animal. Some methods include applying an aqueous liquid to a fungal infection, and then applying a dressing comprising a source of hydrogen peroxide. Some methods include applying a peroxidase enzyme to the infected body surface, and then applying a dressing comprising a source of hydrogen peroxide.

DETAILED DESCRIPTION

Figure 1:
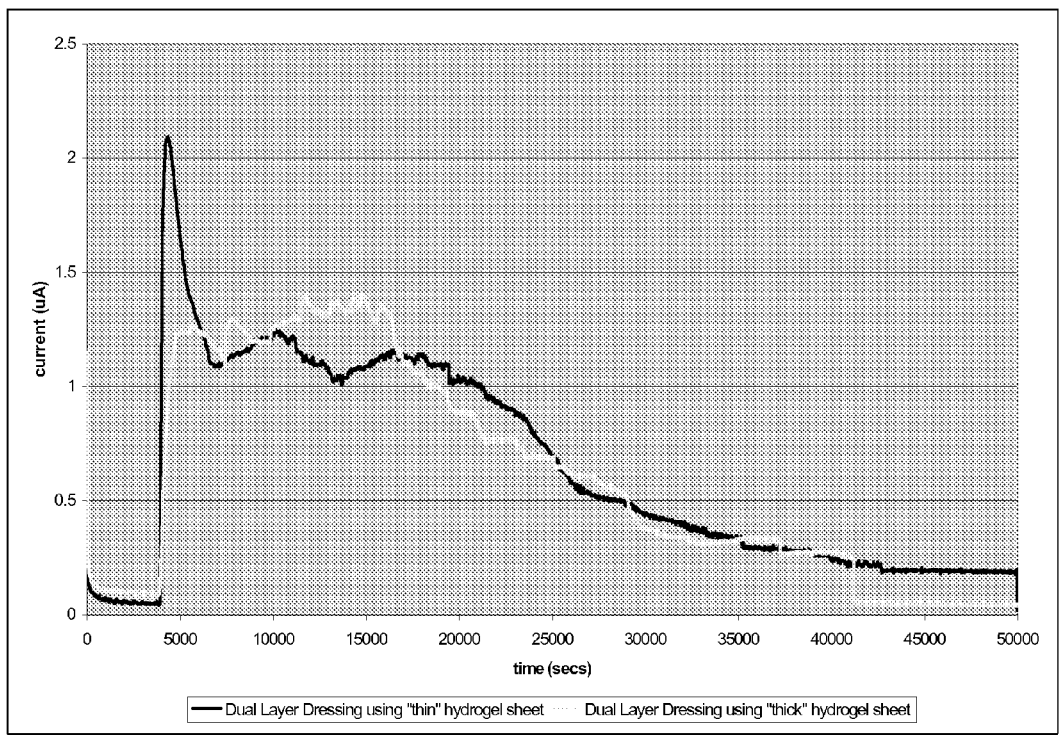
FIG. 1 is a chart showing measured current versus time showing hydrogen peroxide generation.

In a first aspect, the invention relates to a method of treatment of a human or animal body surface infection e.g. a fungal infection, comprising applying an aqueous liquid to the infected body surface e.g. the nail region, followed by applying a dressing comprising a source of hydrogen peroxide.

In a second aspect, the invention relates to a combination of an aqueous liquid and a dressing comprising a source of hydrogen peroxide in the treatment of a human or animal body surface infection e.g. a fungal infection, particularly but not exclusively a human or animal nail region.

In a third aspect, the invention relates to the use of a combination of an aqueous liquid and a dressing comprising a source of hydrogen peroxide in the manufacture of a medicament for the treatment of a human or animal body surface infection e.g. a fungal infection, particularly but not exclusively a human or animal nail region.

By applying an aqueous liquid to the infected body surface, the body surface softens, and becomes more porous. For example, this can allow the liquid to pass into the interior of the nail region via the existing porosity. Thus the liquid provides an aqueous flow path to the interior of the body surface, e.g. nail region.

Subsequent application of a dressing comprising a source of hydrogen peroxide thus results in effective diffusion of the hydrogen peroxide along the generated aqueous flow path into the inner, less accessible parts of the body surface e.g. nail region, enabling the hydrogen peroxide to penetrate deeply allowing significant reduction or elimination of the infection, e.g. fungal infection in all components of e.g. the nail region.

Nails have a distinctive anatomy and composition which must be appreciated when considering new approaches to therapy aimed at the nail plate and the underlying nail bed, as well as all the associated structures. The most conspicuous part of a nail, the nail plate, consists of a hard keratinised structure, made up from dead, cornified cells (corneocytes), pushed up from the matrix at the base of the nail. Most of the nail plate is semi-transparent, allowing the colour of the blood supply in the dermis to show through, giving a pinkish colour. The nail itself is relatively devoid of moisture but, when exposed to water, it can become relatively hydrated, assuming a softened and flexible state.

The nail wall, a fold of skin that overlaps the sides of the nail, holds the nail plate in place and protects its edges. The only living, reproducing part of the nail is the nail matrix, situated directly below the cuticle. New cells form at this point and continually push forward as they mature to produce the nail plate. The matrix is also supplied with nerves as well as abundant blood vessels to provide the cells with nourishment and oxygen.

The nail plate rests on the nail bed, which is continuous with the matrix. It, too, is abundantly supplied with blood vessels and nerves. Its surface is formed into numerous parallel ridges which dovetail exactly with the ridges on the under surface of the nail plate. The cuticle is the part of the skin epidermis that overlaps the nail. It protects the matrix from invading bacteria and physical damage.

Fungal cells can reside and grow in any parts of these structures and it is important for any treatment to pervade all areas in order to eliminate any residual foci of infection as well as eliminating infection in the main areas of the nail plate.

The term "nail region" is defined herein to comprise the nail plate, nail bed, nail matrix, nail wall and cuticle.

The invention also relates to a method of treatment of human papilloma virus-infected cells, comprising applying an aqueous liquid as defined herein to the infected cells followed by applying a dressing comprising a source of hydrogen peroxide as defined herein.

The invention also relates to a combination of an aqueous liquid as defined herein and a dressing comprising a source of hydrogen peroxide as defined herein in the treatment of human papilloma virus-infected cells.

In a preferred embodiment, the aqueous liquid comprises a peroxidase enzyme. The peroxidase diffuses into the interior of the body surface, e.g. the nail region.

The peroxidase enzyme, once it has penetrated the inner region of the body surface, e.g. nail, remains essentially inactive until hydrogen peroxide diffuses via the aqueous pathway from the dressing. In the presence of peroxidase the oxidative effects of hydrogen peroxide are enhanced.

The peroxidase has thus been found to substantially enhance the activity, particularly antifungal activity, of the hydrogen peroxide because it catalyses the oxidation of vulnerable but essential fungal molecules on or in, the cell membrane and/or cytoplasm of the fungal cells.

Any suitable peroxidase may be employed, including lactoperoxidase, horseradish peroxidase, iodide peroxidase, chloride peroxidase and myeloperoxidase. However lactoperoxidase and horseradish peroxidase are currently preferred.

The concentration of peroxidase enzyme in the aqueous liquid is preferably in the range of from 1 to 1000 μg/ml, preferably from 50 to 1000 μg/ml, more preferably from 100 to 500 μg/ml.

The aqueous liquid also preferably comprises surfactants and/or solvents, which have been found to enhance penetration of the liquid into the body surface, e.g. nail.

The dressing is preferably in a hydrated condition, in order that the hydrogen peroxide may diffuse into the nail region effectively once the dressing is applied. Sufficient water is required in the dressing to form a contact liquid junction between the nail region and the dressing.

Preferably the osmotic strength of the aqueous liquid is the same or similar to that of the liquid in the dressing to enhance desired fluid and solute flows.

The dressing preferably donates water to the nail region in use, achieved by selecting appropriate osmotic properties in known manners.

The material of the dressing may be in the form of hydrogel, a sponge, a foam or some other form of hydrophilic matrix that can hold sufficient water to allow a controlled diffusion path between the dressing and the nail region. Preferably, the dressing will contain solutes that serve to regulate the passage of hydrogen peroxide, e.g. by hydrogen bonding, which may be achieved by appropriate concentrations of polymers, e.g. polysaccharides, including glycosaminoglycans.

The dressing may comprise a moist cotton dressing or may include a structural wick material with moist ingredients. Preferably, however, the dressing includes one or more water based or aqueous gels, also referred to as hydrated hydrogels. Such gels may be formed of a variety of materials and may contain a variety of reagents, as will be discussed below.

Typically the dressing will be in the form of a sheet, layer or film. The dressing may alternatively be in the form of an amorphous gel or lotion, preferably a hydrogel, not having a fixed form or shape, that can be deformed and shaped in three dimensions, including being squeezed through a nozzle. Amorphous gels are typically not cross-linked or have low levels of cross-linking. A shear-thinning amorphous gel may be used. Such a gel is liquid when subjected to shear stress (e.g. when being poured or squeezed through a nozzle) but is set when static.

Suitable hydrated hydrogels are disclosed in WO 03/090800. The hydrated hydrogel conveniently comprises hydrophilic polymer material. Suitable hydrophilic polymer materials include polyacrylates and methacrylates, e.g. as supplied by First Water Ltd in the form of sheet hydrogels, including poly 2-acrylamido-2-methylpropane sulphonic acid (polyAMPS) or salts thereof (e.g. as described in WO 01/96422), polysaccharides e.g. polysaccharide gums particularly xanthan gum (e.g. available under the Trade Mark Keltrol), various sugars, polycarboxylic acids (e.g. available under the Trade Mark Gantrez AN-169 BF from ISP Europe), poly(methyl vinyl ether co-maleic anhydride) (e.g. available under the Trade Mark Gantrez AN 139, having a molecular weight in the range 20,000 to 40,000), polyvinyl pyrrolidone (e.g. in the form of commercially available grades known as PVP K-30 and PVP K-90), polyethylene oxide (e.g. available under the Trade Mark Polyox WSR-301), polyvinyl alcohol (e.g. available under the Trade Mark Elvanol), cross-linked polyacrylic polymer (e.g. available under the Trade Mark Carbopol EZ-1), celluloses and modified celluloses including hydroxypropyl cellulose (e.g. available under the Trade Mark Klucel EEF), sodium carboxymethyl cellulose (e.g. available under the Trade Mark Cellulose Gum 7LF) and hydroxyethyl cellulose (e.g. available under the Trade Mark Natrosol 250 LR).

Mixtures of hydrophilic polymer materials may be used in a gel.

In a hydrated hydrogel of hydrophilic polymer material, the hydrophilic polymer material is desirably present at a concentration of at least 0.1%, preferably at least 0.5%, preferably at least 1%, preferably at least 2%, more preferably at least 5%, yet more preferably at least 10%, or at least 20%, desirably at least 25% and even more desirably at least 30% by weight based on the total weight of the gel. Even higher amounts, up to about 40% by weight based on the total weight of the gel, may be used.

A preferred hydrated hydrogel comprises poly 2-acrylamido-2-methylpropane sulphonic acid (poly AMPS) or salts thereof, preferably in an amount of about 20% by weight of the total weight of the gel.

The source of hydrogen peroxide may comprise hydrogen peroxide per se or hydrogen peroxide in combination with or complexed with another entity. Alternatively the source of hydrogen peroxide may be a hydrogen peroxide generation means.

In a preferred embodiment the source of hydrogen peroxide is a hydrogen peroxide generation means comprising oxidoreductase enzyme, a source of oxygen and a source of substrate for the enzyme. The oxidoreductase enzyme catalyses a reaction of an appropriate substrate with oxygen to produce hydrogen peroxide.

Oxidoreductase enzymes suitable for use in the invention and the corresponding substrates (which are present in blood and tissue fluids) include the following:

| Enzyme | Substrate |
| --- | --- |
| Glucose oxidase | β-D glucose |
| Hexose oxidase | Hexose |
| Cholesterol oxidase | Cholesterol |
| Galactose oxidase | D-galactose |
| Pyranose oxidase | Pyranose |
| Choline oxidase | Choline |
| Pyruvate oxidase | Pyruvate |
| Glycollate oxidase | Glycollate |
| Aminoacid oxidase | Aminoacid |

The currently preferred oxidoreductase enzyme is glucose oxidase. This catalyses reaction of β-D glucose substrate to give hydrogen peroxide and gluconic acid.

A mixture of oxidoreductase enzymes may be used.

The oxidoreductase enzyme and glucose may be intimately blended optionally together with a source of oxygen. The oxygen may be provided by any convenient oxygen donor but a convenient source is atmospheric oxygen.

When the source of oxygen is atmospheric oxygen the dressing preferably comprises discrete first and second layers. The first layer comprises the oxidoreductase enzyme and is located in the vicinity of the outer parts of the dressing, i.e. remote from the nail region in use, where atmospheric oxygen levels are highest. The second layer comprises the source of substrate and is located in the vicinity of the inner parts of the dressing, i.e. adjacent the nail region, so that produced hydrogel peroxide can enter the nail region directly.

A preferred form of the layered embodiment is where both the first and second layers include cross-linked hydrated hydrogels. The hydrogels may be cast around a mechanical reinforcing structure, such as a sheet of cotton gauze or a inert flexible mesh, e.g. to provide a structurally reinforced hydrogel layer or slab.

Alternatively, the first enzyme-containing layer may be in dried condition but placed in fluid communication with the second layer during use, resulting in water migrating to the first layer to hydrate the enzyme.

In the layered embodiment it is preferable that the first layer is relatively thin, i.e. from 0.01 to 2.0 mm and the second layer is relatively thick, i.e. from 0.5 to 5.0 mm. If the first layer is a hydrated hydrogel then it is preferably from 0.1 to 2.0 mm thick. If the first layer is a dry film then it is preferably from 0.01 to 0.1 mm thick.

The ratio of thickness of first layer to that of the second layer is preferably from 1:2 to 1:200, preferably from 1:5 to 1:50, more preferably from 1:5 to 1:20.

The oxidoreductase enzyme may conveniently be immobilised so that it is prevented from migrating towards the second layer.

The substrate, e.g. glucose, may be present in various forms including dissolved within a hydrated hydrogel structure, present as a slowly dissolving solid, or encapsulated within another structure for slow release.

It is preferable to arrange the dressing to have an excess of substrate, so the dressing is able to function in use to generate hydrogen peroxide over an extended period of time, e.g. at least one hour e.g. from 1 to 10 hours or more.

The combination according to the invention is typically a packaged kit comprising a combination of an aqueous solution and a dressing comprising a source of hydrogen peroxide as described above.

The components are typically in sealed, water impervious packages.

EXAMPLES

Experimental Summary

Test discs were soaked in 50% serum containing $10^7$ fungal cells to re-create a high protein environment. They were placed on a gel bed, also containing 50% serum to mimic contact with the nail bed. The discs were dosed with aqueous solutions of either horse radish peroxidase or lactoperoxidase, each set of discs having different dose levels of the enzymes. Control discs were left with no peroxidase of any kind. The experiment was started by applying hydrogen peroxide generating stratified patches (see below) to the surfaces of most of the test discs, and these were left in place for defined periods of time. Some discs were left uncovered as additional experimental controls to determine how well the fungal cells survived when left untreated. At set time-intervals, representative discs were removed for sampling, and the numbers of surviving fungal cells were determined by standard methods. These experiments showed that hydrogen peroxide delivered by the stratified gel patches could kill the fungal cells if left in place for several hours. However, the fungal killing rate was strongly enhanced by the additional presence of peroxidase enzyme in contact with the fungus. The enzyme horse radish peroxidase was more potent than lactoperoxidase, and the effect generally increased with dose.

Example 1

Construction and Evaluation of a Hydrogen Peroxide Donating Stratified Layer Patch in Terms of Hydrogen Peroxide Generation Hydrogen peroxide ($H_2O_2$) generation was measured using electrochemistry (slow chrono technique). A dressing was placed onto a bespoke sensor, a potential applied across the electrodes and the presence of $H_2O_2$ measured.

The dressing was comprised of two layers: (i) the hydrated hydrogel layer and (ii) the dry film activation layer containing glucose oxidase.

Preparation of Layer 1: a hydrogel sheet was prepared as follows:

An aqueous solution of 20% sodium 2-acrylamido-2-methylpropanesulfonic acid (Lubrizol Corporation, 50% aqueous stock solution), 10% glucose (Fisher Scientific, Analytical grade), 0.1% zinc lactate (Aldrich) was prepared. Peg 700 diacrylate (Aldrich) was included as crosslinker and 2-hydroxy-2-methyl propiophenone (Aldrich) as the photo initiator. 6.5 g and 13 g of the solution were dispensed into a 10×10 cm petri dish and subjected to 100 mW/cm$^2$ UV light for 20 seconds.

Preparation of Layer 2: a dry film was prepared as follows:

An aqueous solution of 25% w/w PVA (Gohsenol polyvinyl alcohol, code EG05P supplied by Nippon Gohsei) solution was prepared. In addition, 40.3 mg glucose oxidase (Biocatalysts, 150,000 units/gram)+300 mg histidine (Sigma)+150 mg citric acid (Fisher, Analytical grade)+75 mg potassium iodide (Sigma) were dissolved into 2 ml of analytical grade water (Fisher). 30 g of 25% PVA solution was mixed with the glucose oxidase/histidine/citric acid/potassium iodide solution and allowed to settle to remove any entrapped air bubbles. The mix was then dried down at 50° C. to give a dry film of 40-45 micron thickness.

Electrochemical Analysis:

A bespoke 3 electrode sensor (working, counter and reference) was used for the analysis.

Ezescan instrumentation and software was purchased from Whistonbrook Technologies, Luton, UK. The electrodes were mounted within a Teflon box and placed within a 25° C. incubator. In use, 200 of 0.1M KCl solution was applied to the electrode end of the sensor. 1.5×2 cm sections of the Layer 1 hydrogel sheet (6.5 g and 13 g cast weight) were cut and placed onto the KCl solution, ensuring even contact with the electrodes and that no air bubbles were trapped between the gel and the sensor. The gels were covered to reduce evaporation. A potential of +950 mV was applied across the electrodes and the generated current was recorded. When a steady baseline current was obtained, 1.5×2 cm sections of the dry film were applied to the surfaces of the Layer 1 hydrogel sheets. The current generated was recorded. See FIG. 1.

FIG. 1 demonstrates that when a potential of +950 mV was applied to the Layer 1 hydrogel sheet on the sensor, there is very little measurable background current, thus there is little interference from the materials used in the preparation of the hydrogel at this given potential. After application of the dry enzyme film (at around 4000 seconds on the graph), the glucose oxidase chemistry is activated and $H_2O_2$ is produced, which quickly diffused through the Layer 1 hydrogel to the electrode, where a significant rise in current is measured. This clearly shows that the dual layer system generates $H_2O_2$ within the dual layer system and delivers it to the contact surface. The current generated in relation to the main plateau of the chart (between 5,000 and 13,000 seconds) generally equates to around 0.1% $H_2O_2$ (aq). In addition, the different thicknesses of the Layer 1 hydrogel produced very similar curves, with the exception that the thinner gel (6.5 g of gel per 10×10 cm area) gave a significantly higher peak current (therefore concentration of $H_2O_2$) at the hour of application (around 3000 seconds after activation). The $H_2O_2$ measurement then gradually declines until the curves return to a flat response at around 40,000 seconds (approx. 11 hours) after activation.

Example 2

Preparation of Peroxidase Containing Primer Samples as Aqueous Solutions

A suitable basic carrier for the peroxidase was prepared as follows: 50 mM sodium phosphate buffer pH 6-6.5 was mixed with 0.2% w/w Tween 20 (Sigma) surfactant. To this, peroxidase enzyme was dissolved to give a final concentration of 100 μg/ml.

The carrier formulation may be altered to provide different properties as required. For example, the concentration and type of the buffer salt may be changed to provide a range of buffering limits and to change the pH of the solution, depending upon the application and the optimum pH of the enzyme (e.g. peroxidase) used; the concentration and type of surfactant may be changed to provide different wetting characteristics; additional polymeric thickeners may be included to reduce the flow characteristics of the fluid (e.g. to help prevent the solution from running off the nail once applied); the level of enzyme used may also be altered to allow a stronger or reduced peroxidase mediated action on or within the treated structure. Additional additives also may be incorporated to improve the efficacy of the dressing, for example, antimicrobial agents.

Example 3

Testing the Antifungal Treatment System of the Invention Against *Trichophyton Rubrum* in a Model System An in vitro flat bed static diffusion model was utilised, based upon the techniques described in "In vitro diffusion bed, 3-day repeat challenge 'capacity' test for antimicrobial wound dressings", J. Greenman, R. M. S. Thorn, S. Saad, A. Austin International Wound Journal (2006), 3, 322-329.

The test inoculum was prepared by emulsifying mature surface growth biomass of *Trichophyton rubrum* on potato dextrose agar in Saboraud liquid medium, removing the suspension, vortex mixing, and then allowing large particles to settle out of solution. The resulting suspension was adjusted via spectrophotometry to give a standardised inoculum around $10^7$ cfu $ml^{-1}$, which is sufficiently dense to enable any fungicidal effects to be detected (>$10^3$ cfu reduction is seen as indicative of a cidal effect).

A 100 μl volume of the defined inocula was re-suspended in replicate cellulose discs on the surface of a poly-AMPS test bed (the formulation of which is identical to the Layer 1 hydrogel as described in Example 1, but cast as a 25 g gel sheet per 10×10 cm dish), whereby test products can then be applied (FIG. 1). A two layer dressing was tested. The layers were prepared as described in Example 1. Lactoperoxidase or horse radish peroxidase enzymes were prepared by dissolving in analytical water at the required concentration prior to use. It is thought that lactoperoxidase may potentiate any antifungal effects of the novel topical treatment, and for some of the experimental systems cellulose discs were pre-treated with a lactoperoxidase or horseradish peroxidise solution to ascertain differential effects. The range of proposed experimental test and control conditions is shown in table 1.

The two layer dressings were activated by bringing the two layers together. The hydrogel sheet was placed into contact with the cellulose disc and the dry film then applied to the uppermost surface of the hydrogel sheet. Test beds were incubated at 28° C., and at set time intervals (0, 1, 2, 4 & 24 h); cellulose discs were removed, re-suspended in PBSa, serially diluted and then spiral plated onto Saboraud dextrose agar. After incubation (5 days) the number of dermatophyte survivors at different time points after treatment exposure was determined by colony counting (cfu $disc^{-1}$). The results were graphed and analysed using GraphPad Prism (v.4).

Results

Figure 2:
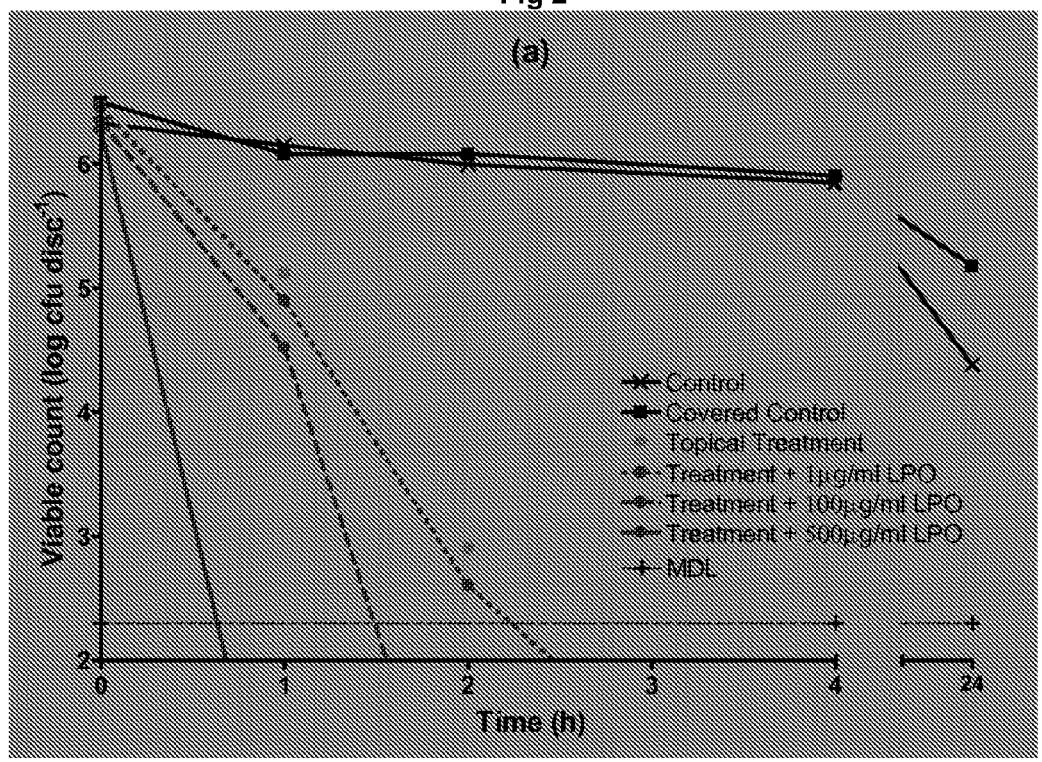
FIG. 2a is a chart showing kill curves of the fungus T. rubrum.
FIG. 2b is another chart showing kill curves of the fungus T. rubrum.
Figure 2:
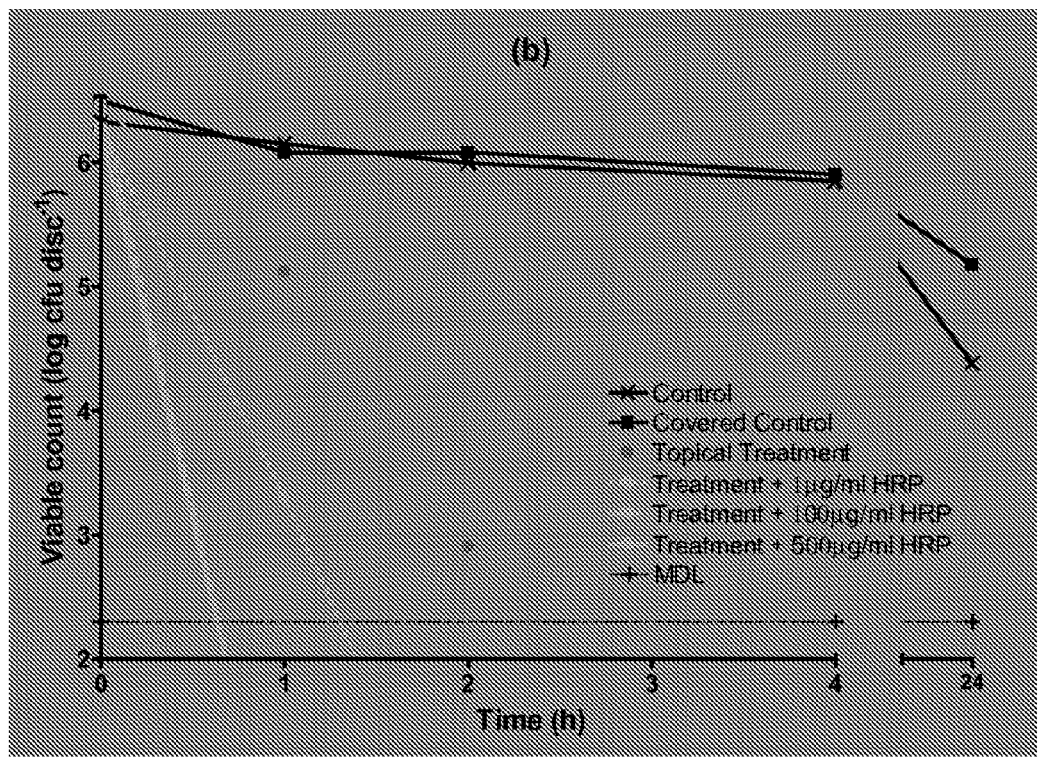

The experimental results are shown in FIG. 2 and it is evident that all test conditions elicited significant antimicrobial effects, and by 3 hours post treatment exposure no viable cells could be detected beneath any of the topical treatments. Lactoperoxidase within the disc appears to potentiate the effects of the topical treatment in a concentration dependant manner, although 1 μg $ml^{-1}$ had no significant effect compared to the test treatment alone (FIG. 2a). Horseradish peroxidise within the disc also potentiates the effects of the topical treatment in a concentration dependent manner, where even the lowest concentration (1 μg $ml^{-1}$) has a significant effect (FIG. 2b). Within control samples there was a slight decline in *T. rubrum* cell numbers, showing that this organism is not very well supported on the fungal test-bed assay plates, particularly after 24 hours incubation; although all test treatments showed significant effects compared to controls. Interestingly it appears that the inactive treatment control is offering some protection to the organism compared to the uncovered control at 24 hours.

CONCLUSIONS

It is evident from the results that the topical treatment alone has a significant antimicrobial effect on *T. rubrum*, reducing viable cell numbers to below the minimum detection point for this system ($2 \times 10^2$ cells) within 3 hours, indicative of a fungicidal effect (>3 log-fold reduction). Both peroxidise and horse radish peroxidise potentiate the effects of the topical treatment, although it is evident that the horseradish peroxidise is more efficacious.

TABLE 1

Experimental test and control conditions for determining the antifungal potential of various novel treatments.

| | |
|---|---|
| Control 1 | Uncovered disc |
| Control 2 | Inactive topical treatment |
| Test 1 | Active topical treatment |
| Test 2 | Active topical treatment + 1 μg/ml lactoperoxidase in disc |
| Test 3 | Active topical treatment + 100 μg/ml lactoperoxidase in disc |
| Test 4 | Active topical treatment + 500 μg/ml lactoperoxidase in disc |

TABLE 1-continued

Experimental test and control conditions for determining
the antifungal potential of various novel treatments.

| Test 5 | Active topical treatment + 1 µg/ml horseradish peroxidase in disc |
| Test 6 | Active topical treatment + 100 µg/ml horseradish peroxidase in disc |
| Test 7 | Active topical treatment + 500 µg/ml horseradish peroxidase in disc |

The invention claimed is:

1. A method of treatment of an infected body surface of a human or animal comprising:
 applying an aqueous liquid to the infected body surface; and
 after applying the aqueous liquid, applying a dressing comprising a source of hydrogen peroxide;
 wherein the body surface infection is a fungal infection.

2. The method of claim 1, wherein the infected body surface is a nail region.

3. The method of claim 1, wherein the aqueous liquid comprises surfactants and/or solvents.

4. The method of claim 1, wherein the dressing is configured to donate water to the infected body surface in use.

5. The method of claim 1, wherein the dressing comprises a hydrated hydrogel material.

6. The method of claim 1, wherein the source of hydrogen peroxide is a hydrogen peroxide generation means comprising an oxidoreductase enzyme, a source of oxygen, and a source of substrate for the oxidoreductase enzyme.

7. The method of claim 6, wherein the oxidoreductase enzyme comprises glucose oxidase.

8. The method of claim 6, wherein the dressing comprises discrete first and second layers, wherein the first layer comprises the oxidoreductase enzyme and is located in outer parts of the dressing, and wherein the second layer comprises the source of substrate for the oxidoreductase enzyme and is located in inner parts of the dressing.

9. The method of claim 1, wherein the aqueous liquid comprises a peroxidase enzyme.

10. The method of claim 9, wherein the peroxidase enzyme comprises lactoperoxidase, horseradish peroxidase, or a mixture thereof.

11. The method of claim 9, wherein the concentration of peroxidase enzyme in the aqueous liquid is in the range of from 1 to 1000 µg/ml.

12. A method of treatment of an infected body surface of a human or animal comprising:
 applying an aqueous liquid to the infected body surface; and
 after applying the aqueous liquid, applying a dressing comprising a source of hydrogen peroxide;
 wherein the aqueous liquid comprises a peroxidase enzyme.

13. The method of claim 12, wherein the peroxidase enzyme comprises lactoperoxidase, horseradish peroxidase, or a mixture thereof.

14. The method of claim 12, wherein the concentration of peroxidase enzyme in the aqueous liquid is in the range of from 1 to 1000 µg/ml.

15. The method of claim 12, wherein the infected body surface is a nail region.

16. The method of claim 12, wherein the aqueous liquid comprises surfactants and/or solvents.

17. The method of claim 12, wherein the dressing is configured to donate water to the infected body surface in use.

18. The method of claim 12, wherein the dressing comprises a hydrated hydrogel material.

19. The method of claim 12, wherein the source of hydrogen peroxide is a hydrogen peroxide generation means comprising an oxidoreductase enzyme, a source of oxygen, and a source of substrate for the oxidoreductase enzyme.

20. The method of claim 19, wherein the oxidoreductase enzyme comprises glucose oxidase.

21. The method of claim 19, wherein the dressing comprises discrete first and second layers, wherein the first layer comprises the oxidoreductase enzyme and is located in outer parts of the dressing, and wherein the second layer comprises the source of substrate for the oxidoreductase enzyme and is located in inner parts of the dressing.

* * * * *